United States Patent [19]
Schick

[11] Patent Number: 5,434,418
[45] Date of Patent: Jul. 18, 1995

[54] INTRA-ORAL SENSOR FOR COMPUTER AIDED RADIOGRAPHY

[76] Inventor: David Schick, 150-54 76th Rd., Flushing, N.Y. 11367

[21] Appl. No.: 962,129

[22] Filed: Oct. 16, 1992

[51] Int. Cl.$^6$ .......................... G01T 1/24; A61B 6/14
[52] U.S. Cl. ...................... 250/370.11; 250/370.09; 378/191
[58] Field of Search ............ 250/370.11, 370.09; 378/191

[56] References Cited

U.S. PATENT DOCUMENTS

| | | | |
|---|---|---|---|
| 4,069,438 | 1/1978 | Houston et al. | 250/213 VT |
| 4,160,997 | 7/1979 | Schwartz | 378/191 |
| 4,179,100 | 12/1979 | Sashin et al. | 250/370.09 |
| 4,593,400 | 6/1986 | Mouyen | 378/191 |
| 4,987,307 | 1/1991 | Rizzo et al. | 250/370.11 |
| 5,187,369 | 2/1993 | Kingsley | 250/370.11 |
| 5,187,380 | 2/1993 | Michon et al. | 250/370.11 |

FOREIGN PATENT DOCUMENTS

| | | | |
|---|---|---|---|
| 58230 | 8/1992 | European Pat. Off. | 250/370.11 |

*Primary Examiner*—Carolyn E. Fields
*Attorney, Agent, or Firm*—Israel Nissenbaum

[57] ABSTRACT

An intra-oral sensor for computer aided oral examination by means of low dosage x-rays in place of film and developer. The intra-oral sensor is exceedingly thin for proper mouth placement and in situ maneuvering, with an active area substantially equivalent to corresponding dental film sizes and a thickness of no more than about 3 mm. In addition, the sensor contains limited electronics and no optical elements, and is resistant to moisture and heat and is readily autoclaved. The sensor, consists of a thin, large area semiconductor image array such as a modified charge coupled device (CCD) or photodiode array, coated with a thin, epitaxial growth of a material such as thallium doped cesium iodide CsI(Tl). The coated sensor is bonded to and supported on a passivated ceramic chip, and has an integrated signal amplifier, with the entire assembly being coated with a protective inert plastic layer, e.g., polytetrafluoroethylene, which is pervious to x-ray radiation. The CsI(Tl) is sensitive to x-ray photons, efficiently converting them into visible photons in the 500–600 um range. To reduce light spreading within the CsI(Tl) layer, growth of the CsI(Tl) layer is directed into narrow (20 um) columns. Visible photons are detected by the large area semiconductor array and the output is monitored by a computer until polling of the CCD or photodiode array indicates that there is no further conducting. A signal thereafter causes a read out of the electrical charges for translation from analog to digital signals of images with computer display and analysis.

2 Claims, 2 Drawing Sheets

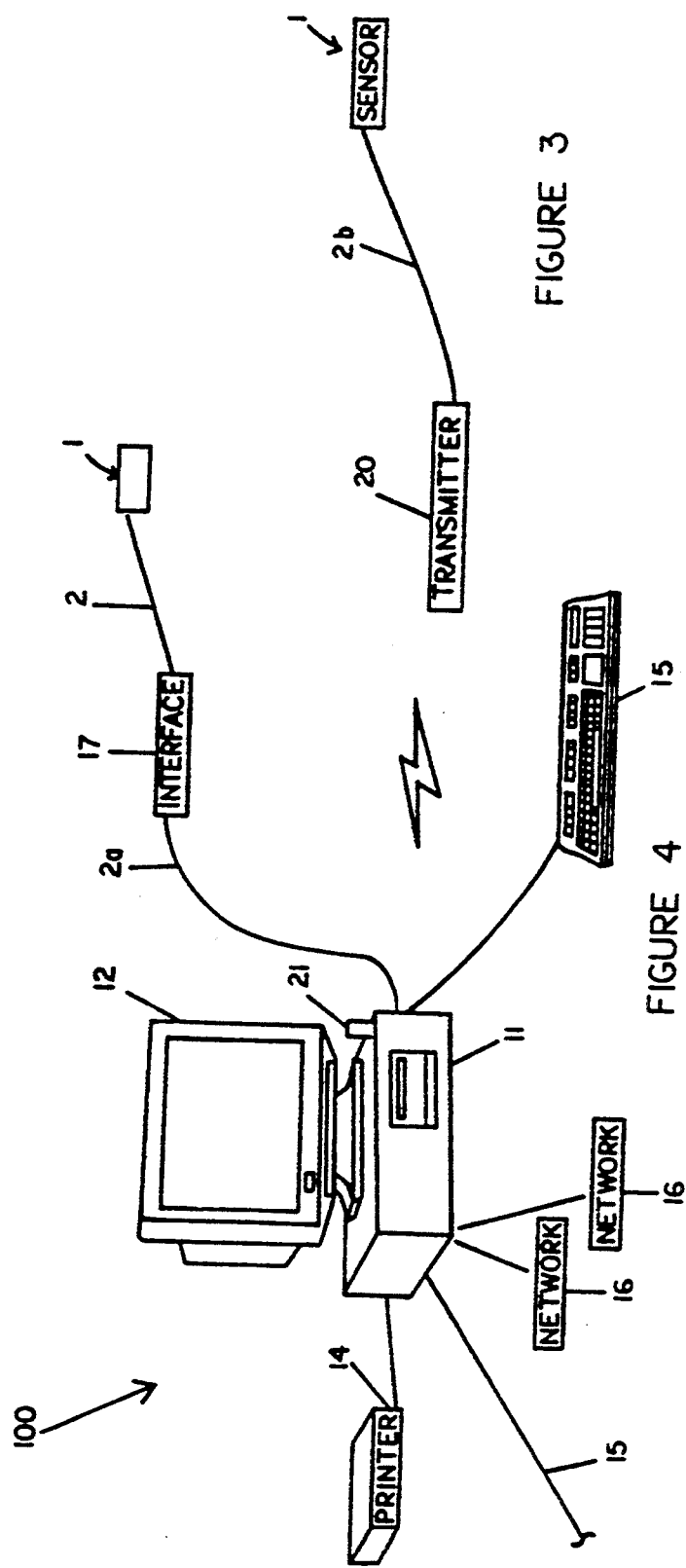

INTRA-ORAL SENSOR FOR COMPUTER AIDED RADIOGRAPHY

FIELD OF THE INVENTION

This invention relates to oral and dental radiology and particularly to computer aided radiology without use of x-ray film.

BACKGROUND OF THE INVENTION

Dentists and oral surgeons typically utilize x-ray apparatus to examine patients prior to treatment. Film placed in the patient's mouth is exposed to the x-rays which pass through the soft tissue of skin and gums and are absorbed or refracted by the harder bone and teeth structures. The film is then chemically developed and dried to produce the image from which the dentist makes appropriate treatment; evaluations. Such technology, though with many refinements, has not basically changed over the past fifty years.

Though the technology is a mature one and well understood in the field, there are numerous drawbacks in conventional dental radiology which utilizes film for image capturing. Foremost among such problems is the radiation dosage, which optimally for conventional film exposure, is about 260 millirads. Since the high energy electrons from x-ray sources can cause damage to the nuclei of cells it is agreed that minimizing radiation exposure is highly desirable. In this regard, the average dose for dental x-rays has been reduced by 50% over the last thirty years, to the current levels, mostly as a result of improvement in film sensitivity. Further incremental reductions in requisite x-ray dosage for film exposure is unlikely to be of any great extent.

Film processing itself presents other problems including the time, expense, inconvenience and uncertainty of processing x-ray films and many times the exposure is defective or blurred. The minimum time for development is four to six minutes. In addition, there is the cost and inconvenience of storing and disposing of the developing chemicals which are usually environmentally harmful.

To obviate these problems, various expedients have been proposed or developed for the purpose of x-ray imaging without film. The general principal in all of such expedients has been the conversion of x-ray radiation into visible light by scintillators and conversion of the light into electrical video signals for viewing or into electrical signals for printing. Representative of such expedients are U.S. Pat. No. 4,160,997, issued to Robert Schwartz; U.S. Pat. No. 4,593,400, issued to Francis Mouyen; and U.S. Pat. No. 4,987,307, issued to Giorgio Rizzo and Cesare Gadda. All of such patents, and others in the field, embodied sensors which included phosphor scintillator screens and separated and distinct CCD elements for conversion of light to electrical signals. The CCD elements, because of limitations in capability and sensitivity to hard x-rays, required additional light processing enhancing and x-ray shielding components in the sensor. Examples of such additional components include the pyramidal optical fiber containing screen of Mouyen, specifically used to obviate problems with the Schwartz sensor, and the micro-lens system of Rizzo et al., specifically described as obviating problems with optical fiber containing sensors.

As a result of the various "improvements" the sensors of the prior art were relatively bulky compared to dental x-ray film. Mouyen, for example, describes his sensor as being up to 17 mm thick. This presents problems in proper oral placement and manipulation in adult patients and severely restricts pediatric use.

Furthermore, the additional components entail greater costs, introduce problems with component degradation and failure, and generally preclude direct sterilization by dental autoclaving. The sensors of the prior art are accordingly usually described as being used with disposable plastic sleeves. However, such sleeves while useful, may be occasionally susceptible to perforation during use, a dangerous situation with prevalent communicable diseases.

Finally, the systems described provided resolution of images substantially below that of x-ray dental film. Thus, though x-ray dosage is reduced, it is at the cost of diagnostic accuracy.

SHORT DESCRIPTION OF THE INVENTION

It is an object of the present invention to provide an intra-oral sensor with a thickness of less than 5 mm for computer aided oral radiography which simulates the optimal active areal dimensions of x-ray films.

It is a further object of the present invention to provide such intra-oral sensor which can be safely sterilized by dental autoclaving.

It is a still further object of the present invention to provide an economical, simplified sensor and signal processing system for converting x-rays, at dosages of less than 25 millirads, into dental images diagnostically superior to that of dental film.

It is another object of the present invention to provide the intra-oral sensor whereby it is minimally degraded by x-rays.

These and other objects, features and advantages of the present invention will become more obvious from the following discussion and drawings in which:

SHORT DESCRIPTION OF THE DRAWINGS

FIG. 3 shows the sensor of FIG. 1 and 2 connected to a small radio transmitter for image transmission to a remote computer; and FIG. 4 is a schematic view showing the utilization of the sensor of the present invention in a computerized dental diagnostic system.

DETAILED DESCRIPTION OF THE INVENTION

Figure 1:
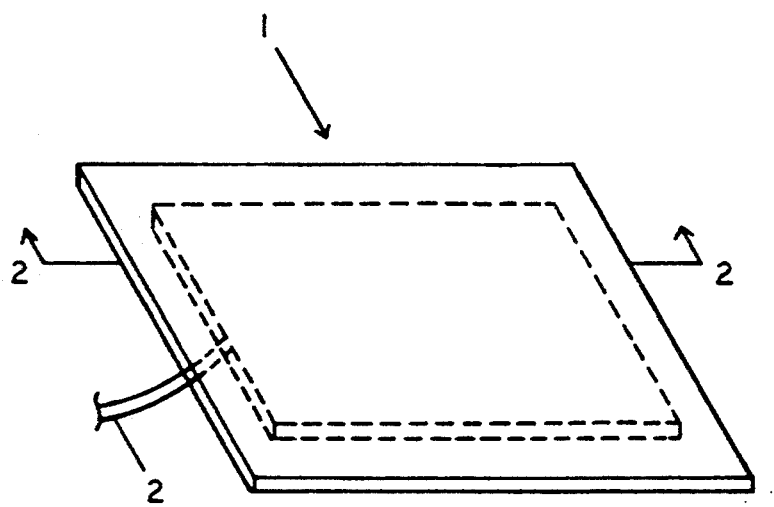
FIG. 1 is an isometric view of the sensor of the present invention.

Generally, the present invention comprises an intra-oral sensor for computer aided oral radiography, comprising a thin, large area semiconductor image array, such as a modified charge coupled device (CCD) or photodiode array, coated with a thin, epitaxial growth of a material, such as thallium doped cesium iodide CsI(Tl), which provides conversion of x-rays to light or visible photons; and said semiconductor image array converts the light or visible photons to electrical signals for transmission to computer means for imaging. The imaging can be in the form of real time monitor viewing and/or as a hard copy printout. The coating material also provides protection to the semiconductor image array from x-ray degradation.

In preferred embodiments, the coated sensor contains an integrated signal amplifier, and is bonded to and supported on a passivated ceramic chip, with the entire assembly being coated with a protective (particularly against moisture) inert plastic layer, e.g., polytetrafluoroethylene (PTFE), which is pervious to x-ray radiation. The CsI(Tl) is sensitive to x-ray photons, efficiently converting them into visible photons in the 500-600 um range. Other x-ray-to-light converting materials, though of lesser efficiency, include cadmium telluride and cadmium sulfide, calcium tungstate ($CaWO_4$), zinc sulfide and zinc cadmium sulfide.

To reduce light spreading within the CsI(Tl) layer, growth of the CsI(Tl) layer is preferably directed into narrow (10-20 um) Columns. With CsI(Tl) thicknesses of 300 um or more it is further preferred that a laser be utilized to make channels between the columns in order to eliminate cross-talk in the computerized imaging. Light and/or visible photons are detected by the large area semiconductor array and the output is monitored by a computer until polling of the CCD or photodiode array indicates that there is no further conducting. A signal thereafter causes a read out of the electrical charges, for translation from analog to digital signals of images, with computer display and analysis.

The intra-oral sensor is exceedingly thin for proper mouth placement and in situ maneuvering, with a large active area substantially equivalent to corresponding dental film sizes. Such proper mouth placement dictates a maximum thickness of about 5 mm and more preferably a thickness of no more than about 3 mm. One common size of dental film has an active area of approximately 4×3 cm, corresponding to size 2 dental film which is commonly used for adult radiographs. Another dental film with an active area of approximately 3.2×2.4 cm is size 0 dental film, the standard pediatric film size. In addition to large active areas and thin dimensions, the sensor contains limited electronics and no optical elements, is resistant to moisture and heat, and is readily autoclaved.

In order to reduce radiation effects on the sensor in the form of spurious signals caused by penetration of the x-rays into the silicon of the semiconductor layer, two means may be utilized. Firstly, the CsI layer is grown in a relatively thick layer of 200-300 um on the active portion of the semiconductor. This reduces the probability of x-ray photons from impinging on the silicon of the semi-conductor to less than 0.01%. To compensate for reduction in x-ray photons, spatial resolution is maintained by carefully growing high quality CsI layers.

Secondly, the CCD may be formed on a thin (10 um) epitaxial silicon layer with p type doping, grown on a $p^+$ doped bulk silicon wafer. This process provides that only the x-rays which are absorbed by the epitaxial layer can contribute to the image. Since silicon is a very poor absorber of x-rays of average energy of 35 KeV, very few x-rays (less than 0.1%) will be absorbed in the top 10 um of the silicon.

In order to reduce the performance degradation of the CCD due to long-term exposure to x-rays, the CCD is preferably operated in Multi-Phase Pinned (MPP) mode. Normally, the primary long-term effect of radiation such as x-rays on CCDs is an increase in dark signal from thermally generated electron hole pairs. These hole pairs increase with the introduction of a trap level near the surface of the silicon by accumulated x-rays. The dark signal reduces the sensitivity of the CCDs and lowers the maximum exposure to which they can respond. By using the MPP mode operation, the surface of the semiconductor is "pinned" by keeping the potential at the surface negative for a great portion of the time. As a result, thermally generated electron hole pairs at the surface are exterminated before they cause a signal.

In both embodiments of CCD and photodiode semiconductor arrays, the sensor comprises a self-scanning array with a maximum pixel size of 48 um. The array contains (on-chip) all of the circuitry required to control the exposure and read-out of the image. As with the CCD embodiment, the photodiode array is coated with a thin layer of thallium doped cesium iodide, CsI(Tl), to convert the x-ray photons into visible photons in the 500-600 um range which are efficiently absorbed by the photodiodes.

Each of the CCD and photodiode arrays incorporates several discrete diodes, the outputs of which are monitored by the computer to determine the start and end of the exposure. This method allows for accurate exposures to be taken without the need to synchronize the x-ray source with the computer.

The CsI is preferably applied to the surface of the CCD or photodiode array via a vacuum-evaporation process which is optimized to prevent light-spreading within the layer. The surface of the CCD or photodiode array is first preferably prepared by immersing it in a plasma-gas in order to promote adhesion. A thin, radio-opaque, light transmitting material may be deposited onto the array in order to prevent any transmitted high-energy photons from impinging on the CCD or photodiodes. Then the CsI is grown onto the array in such a way as to form the narrow columns which prevent the light from spreading within the CsI layer. The layer is covered with an oxide which is grown on top of the CsI to prevent moisture from being absorbed. The array is then bonded onto a thin ceramic which is attached to an insulator (e.g. PTFE) coated electrical cable and the chip area is passivated with an electrically insulating opaque sealant. The assembly is then coated with PTFE or some other plastic to protect against stress, shock and moisture.

The electrical cable may extend directly to the computer for the direct input of the electrical imaging signals. Alternatively, in order to prevent entanglement or tripping over wires, the cable is short and extends to a short range radio transmitter for transmission of the electrical imaging signals to the computer. The short cable is preferably detachable from the transmitter for autoclaving of the sensor.

In operation, the intra-oral sensor translates the x-rays to light which then generates an analog signal. The analog signal then causes a read out of the electrical charges for translation from analog to digital signals of images with computer display and analysis. The sensor is attached via the thin, flexible PTFE cable to an interface box, which is connected to the computer. The interface box digitizes the analog video signal from the sensor and transmits it to the computer for the display and analysis.

The computer, and associated peripherals, used to acquire the images from the sensor, preferably incorporates at least the following elements:

(a) A CPU with sufficient power to execute digital signal processing (DSP) routines on the images without noticeable time-lag.
(b) A removable disk sub-system to store the images.
(c) A high-resolution display system which can display colors and at least 256 shades of grey.

(d) A printer which can reproduce an entire image with at least 256 shades of grey.

(e) A keypad and pointing device to act as an operator interface.

Optional devices for additional enhancements include:

(a) A high-speed modem to transmit x-ray image data in order to take full advantage of automatic insurance claims processing. At present, all parts of the claims process may be sent via modem except for x-ray documentation, which must be sent via mail and then returned.

(b) A write once optical-disk subsystem for mass storage of images.

(c) A local-area network to connect more than one system within an office.

Software for operation of the system includes software which allows the dentist an easy and intuitive method of taking the x-rays, organizing and viewing them, and storing and recalling them. On a low-level, the software controls the sensor operation and other system functions. The software also includes a set of algorithms for manipulating the images via:

(a) Image compression routines with variable compression rate and image quality.

(b) Filter routines for noise elimination and feature enhancement.

(c) Contrast equalization, expansion and adjustment algorithms.

(d) Viewing routines for zooming and panning.

The normal exposure sequence is conducted as follows:

(a) The dentist positions the sensor in the patient's mouth and sets the computer to begin monitoring.

(b) The computer holds the array in a reset mode which clears all of the pixels and begins polling the discrete photodiodes.

(c) As soon as the exposure begins, the computer senses current across the diodes. The array is placed in an exposure mode in which the pixels are allowed to integrate the accumulated charge.

(d) When the exposure ends the computer senses that the diodes are not conducting. A clock signal is applied to the array to read out the image.

DETAILED DESCRIPTION OF THE DRAWINGS AND THE PREFERRED EMBODIMENT

With specific reference to the drawings, in FIG. 1 sensor 1 is shown proportioned for adult use and the dotted lines indicate the proportioned size for pediatric use. Cable 2 transmits the analog signal from the sensor 1 from within the patient's mouth and is adapted to retain integrity and inertness with such utilization.

Figure 2:
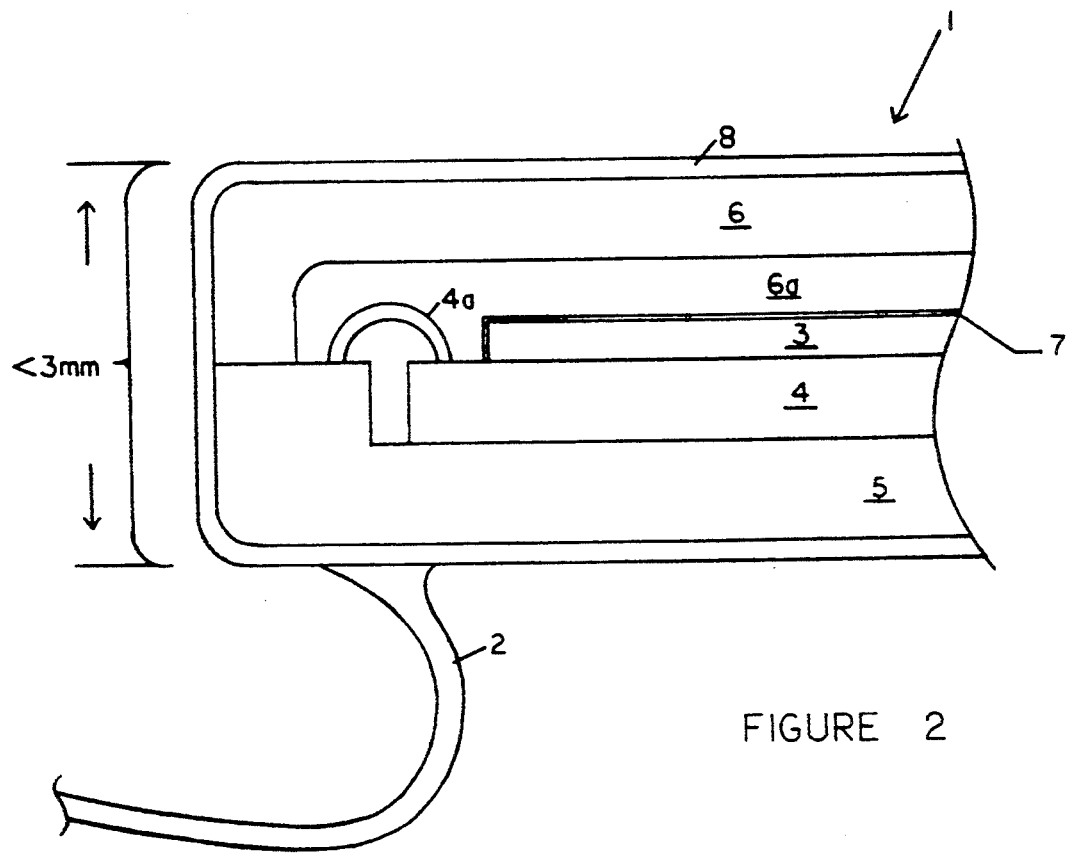
FIG. 2 is a magnified cross sectional view of the sensor of FIG. 1 taken along line 2—2.

As shown in FIG. 2, the x-ray active area of semiconductor 4 is coated with a thallium doped cesium idodide layer 3 for conversion of x-rays to light or visible photons. The semiconductor 4, in turn converts the light to electrical signals which represent the x-ray image. Layers 6 and 6a of epoxy and silicone respectively provide physical protection to the coated semiconductor. The various layers of the sensor 1 provide an overall thickness of no more than about 3 mm, comparable to standard x-ray film with protective retaining elements. The entire sensor is enclosed by protective PTFE layer 8. Protective layer 8 and epoxy coat 6 enable the sensor to be moisture resistant and autoclavable. Silicone layer 6a provides a resilient match between the coated semiconductor and protective epoxy coat 6 which are of different coefficients of expansion. Silicone layer 6a thereby prevents delamination of the epoxy coat from the coated semiconductor, during autoclave heating. The thickness of the PTFE layer 8 is sufficient to resist tears by a patient's teeth. The x-ray-to-light converting layer 3 of thallium doped CsI, is positioned to be directly exposed to the x-rays which readily pass through protective PTFE layer 8, epoxy coat 6 and silicone layer, 6a. The CsI layer 3 is interposed between the x-ray source and active portion of the semiconductor layer (CCD or photodiode) 4 to both protect the semiconductor from degradation from x-ray exposure and to provide conversion of the x-rays to visible light for direct detection by the semiconductor. A very thin oxide layer 7, on the CsI layer 3 further protects against moisture degradation.

The semiconductor layer 4 is supported on passivated ceramic chip 5 with semiconductor 4 further having integrated signal amplifier means therein for amplification of the analog signal from the semiconductor via conductive lead 4a, to the computer analysis and display system 100 (shown in FIG. 4), via cable 2.

The analog signal from the sensor 1 enters interface box 17 which digitizes the signal for computer processing by CPU unit 11. The digitized signal is thereafter directly carried by cable 2a to the CPU unit 11, or as shown in FIG. 3, the digitized signal is carried by short (14″ or 36 cm) cable 2b to short range radio transmitter 20 (with internal analog to digital converter) for transmission to receiver 21 and then to CPU 11.

In either embodiment, the sensor 10 and attached cable 2 are autoclavable with cable 2 being detachable from interface box 17 and radio transmitter 20. The processing can be made available on a network 16 or to a single output device such as monitor 12 and/or printer 14. Appropriate instructions and manipulation of image data is effected via keyboard or input control 13. X-ray images can thereafter be efficiently directly transmitted to remote insurance carrier computers via an internal modem (not shown) and standard telephone line 15.

It is understood that the above description and drawings are illustrative of the present invention and details contained therein are not to be construed as limitations on the present invention. Changes in components, procedure and structure may be made without departing from the scope of the present invention as defined in the following claims.

What is claimed is:

1. An x-ray signal imaging system for dental radiography comprising an intra-oral sensor for computer aided oral examination comprising a semiconductor image array coated with a layer of a material which absorbs and converts x-rays to visible photons; said semiconductor image array comprising means for converting the visible photons to electrical signals suitable for transmission to computer means for imaging; said system further comprising said computer means and transmission means for transmission of the electrical signals to the computer means, which processes the electrical signals for visual imaging; and visual imaging means for providing a viewable image of an x-ray image; with said imaging system further comprising signal processing means for conversion of said electrical signals from analog to digital form prior to said transmission; wherein said semiconductor image array is comprised of pixels, and said semiconductor image array is comprised of discrete photodiodes, and wherein the computer means further comprises polling means, with said computer means being adapted to hold the array in a reset mode to clear all of the pixels of the semiconductor image array and the polling means polling the discrete photodiodes, and wherein, with the beginning of exposure of the semiconductor image array to x-rays, the computer means comprises sensing means to sense current across the photodiodes whereby the computer means is able to place the semiconductor image array in an exposure mode in which the pixels are allowed to integrate accumulated charge, and when the exposure ends the computer means senses that the diodes are not conducting, with the computer means further comprising clock means to thereafter apply a clock signal to the array to read out the image via the electrical signals.

2. A method for operating an x-ray signal imaging system comprising an intra-oral sensor for computer aided oral examination; said sensor comprising a semiconductor image array coated with a layer of a material which absorbs and converts x-rays to visible photons, said semiconductor image array comprising means for converting the visible photons to electrical signals suitable for transmission to computer means for imaging, wherein said semiconductor image array is a CCD, said method comprising the steps of operating the CCD in a multi-phase pinned (MPP) mode wherein the surface of the CCD is pinned; keeping the potential at an x-ray exposed surface of the CCD negative for a period of the time whereby thermally generated electron hole pairs at the surface are exterminated before they cause a signal; thereafter converting said electrical signals from analog to digital form and transmitting the electrical signals to computer means which process the electrical signals for visual imaging.

* * * * *